United States Patent
Navarro de Lara et al.

(10) Patent No.: US 9,924,889 B2
(45) Date of Patent: Mar. 27, 2018

(54) METHOD AND SYSTEM FOR COMBINED TRANSCRANIAL MAGNETIC SIMULATION (TMS) AND FUNCTIONAL MAGNETIC RESONANCE IMAGING (FMRI) STUDIES

(71) Applicants: Lucia Isabel Navarro de Lara, Vienna (AT); Christian Windischberger, Vienna (AT); Elmar Laistler, Vienna (AT); Jürgen Sieg, Vienna (AT); Ewald Moser, Vienna (AT); André Kühne, Vienna (AT)

(72) Inventors: Lucia Isabel Navarro de Lara, Vienna (AT); Christian Windischberger, Vienna (AT); Elmar Laistler, Vienna (AT); Jürgen Sieg, Vienna (AT); Ewald Moser, Vienna (AT); André Kühne, Vienna (AT)

(73) Assignee: MEDICAL UNIVERSITY OF VIENNA, Vienna (AT)

( * ) Notice: Subject to any disclaimer, the term of this patent is extended or adjusted under 35 U.S.C. 154(b) by 676 days.

(21) Appl. No.: 14/045,429

(22) Filed: Oct. 3, 2013

(65) Prior Publication Data
US 2015/0099963 A1 Apr. 9, 2015

(51) Int. Cl.
*A61B 5/05* (2006.01)
*A61B 5/055* (2006.01)
(Continued)

(52) U.S. Cl.
CPC ........ *A61B 5/055* (2013.01); *G01R 33/34084* (2013.01); *G01R 33/3415* (2013.01); *G01R 33/4806* (2013.01); *G01R 33/4808* (2013.01)

(58) Field of Classification Search
CPC ....................................................... A61B 5/05
See application file for complete search history.

(56) References Cited

U.S. PATENT DOCUMENTS

| 5,732,702 A | 3/1998 | Mueller |
| 6,179,771 B1 * | 1/2001 | Mueller .................. 600/13 |

(Continued)

FOREIGN PATENT DOCUMENTS

| EP | 1714162 | 10/2006 |
| WO | WO 2005109010 | 11/2005 |

OTHER PUBLICATIONS

"A TMS coil positioning/holding system for MR image-guided TMS interleaved with fMRI" by D.E. Bohning et al. Clinical Neurophysiology. 114. (2003) pp. 2210-2219.*

(Continued)

*Primary Examiner* — Tse Chen
*Assistant Examiner* — Jason Ip

(57) ABSTRACT

A method for transcranial magnetic stimulation (TMS) of a stimulation area of medical interest, combined with functional magnetic resonance imaging (fMRI) for visualization of the response of, for example neurons, is disclosed. An ultra-thin magnetic resonance coil, MR coil, positioned in the immediate vicinity over an area where the response of, for example neurons, is to be detected, and preferably sandwiched between the TMS coil and the area, provides an excellent signal-to-noise ratio. The TMS can be performed directly through the MR coil. A great deal of flexibility in the number of the TMS and MR coils in use and their spatial arrangement is provided. A corresponding system for the TMS/fMRI studies is also provided.

20 Claims, 14 Drawing Sheets

(51) Int. Cl.
*G01R 33/34* (2006.01)
*G01R 33/3415* (2006.01)
*G01R 33/48* (2006.01)

(56) References Cited

U.S. PATENT DOCUMENTS

| | | | |
|---|---|---|---|
| 6,198,958 B1 | 3/2001 | Ives et al. | |
| 6,488,617 B1 | 12/2002 | Katz | |
| 7,701,209 B1 | 4/2010 | Green | |
| 7,826,887 B2 * | 11/2010 | Driemel | 600/422 |
| 2007/0159176 A1 | 7/2007 | Lanz et al. | |
| 2007/0262777 A1 * | 11/2007 | Warntjes et al. | 324/318 |
| 2007/0282194 A1 * | 12/2007 | Wiggins et al. | 600/422 |
| 2010/0113959 A1 | 5/2010 | Pascual-Leone et al. | |
| 2011/0241683 A1 * | 10/2011 | Nnewihe et al. | 324/318 |
| 2013/0123609 A1 | 5/2013 | Odoj et al. | |

OTHER PUBLICATIONS

Moisa, M., et al, (2009), New coil positioning method for interleaved transcranial magnetic stimulation (TMS)/functional MRI (fMRI) and its validation in a motor cortex study. Journal of magnetic resonance imaging : JMRI, 29(1), 189-97.
Bohning, D. E., et al, (2003), A TMS coil positioning/holding system for MR image-guided TMS interleaved with fMRI. Clinical Neurophysiology, 114(11), 2210-2219.
Bohning DE, et al, (1999), A combined TMS/fMRI Study of intensity-dependent TMS over motor cortex. Biological Psychiatry, 45:385-394.
Kaggie, Joshua D., et al, A 3T Sodium and Proton Breast Array, Proc. Intl. Soc. Mag,. Reson. Med. 21 (2013), 4010, 1 page.
Duan, Yunsuo, et al, A 16-Element Highly Flexible RF Array Coil for 3T MRI, Proc. Intl. Soc. Mag,. Reson. Med. 21 (2013), 4383, 1 page.
Driver, Jon, et al, Concurrent Brain-Stimulation and Neuroimaging For Studies of Cognition, Trends in Cognitive Sciences, vol. 13, No. 7, Jun. 18, 2009, 319-327.
Griswold, M. A., et al, (2002). Generalized Autocalibrating Partially Parallel Acquisitions (GRAPPA). Magnetic Resonance in Medicine, 47(6), Wiley-Liss, Inc. 2002, 1202-1210.
Kobayashi, Masahito, et al, Transcranial Magnetic Stimulation in Neurology, The Lancet Neurology, vol. 2, Mar. 2003, 145-156.
Pruessman, K. P., et al, (1999). SENSE: Sensitivity Encoding for Fast MRI. Magnetic resonance in medicine, 42(5), Wiley-Liss, Inc. 1999, 952-962.
Barker AT, et al, Non-invasive magnetic stimulation of the human motor cortex. Lancet 1985; 1:1106-1107.
Curra A, et al, Trannscranial magnetic stimulation techniques in clinical investigations. Neurology 2002; 59:1851-1859.
Hallet M, Transcranial magnetic stimulation and the human brain. Nature 2000; 406:147-50.
Mills KR., Magnetic stimulation of the human nervous system. Oxford: Oxford University Press; 1999.
Walsh V, et al, Transcranial magnetic stimulation: a neurochronometrics of mind. Cambridge, MA: MIT Press; 2005.
Rothwell JC., Techniques and mechanisms of action of transcranial magnetic stimulation of the human motor cortex. J Neurosci Methods 1997; 74: 113-122.
Rossini PM, et al (2007) Transcranial magnetic stimulation: diagnostic, therapeutic, and research potential. Neurology; 68: 484-488.
Chen, R., et al, (2008) The clinical diagnostic utility of transcranial magnetic stimulation: report of an IFCN committee. Clinical neurophysiology official journal of the International Federation of Clinical Neurophysiology. 119(3), 504-532.
George MS, Wassermann EM. (1994) Rapid-rate transcranial magnetic stimulation (rTMS) and ECT. Convuls Ther; 10(4): 251-253.
George MS, et al. (1995) Daily repetitive transcranial magnetic stimulation (rTMS) improves mood depression. Neuroreport.vol. 6: 1853-1856.
Pascual-Leonea, et al, (1996) Beneficial effect of rapid-state transcranial magnetic stimulation of the left dorsolateral prefrontal cortex in drug resistant depression. The Lancet, 348, 233-237.
Figiel, GS, et al. (1998) The use of rapid rate transcranial magnetic stimulation (rTMS) in refractory depressed patients. J Neuropsychiatry Clin Neurosci, 10:20-25.
Bohning DE, et al. (1998) Echoplanar BOLD fMRI of brain activation induced by concurrent transcranial magnetic stimulation. Invest Radiol;33:336-340.
Reykowski, A., et al (1995). Design of matching networks for low noise preamplifiers. Magnetic Resonance in Medicine, 33, 848-852.
Seeber, D. et al, (2004). Floating shield current suppression trap. Concepts in Magnetic Resonance Part B: Magnertic Resonance Engineering, 21B(1), 26-31. doi:10.1002/cmr.b.20008.
Siemens, Phased Array, MR Coil, Sep. 30, 2013.
Navarro De Lara, Lucia Isabel, Design of an Ultra-Slim 7-Channel Receive-Only Phased-Array Head Coil Dedicated for Combined TMS and fMRI Experiments, 29th Annual Meeting of the ESMRMB (European Society for Magnetic Resonance in Medicine and Biology), Lisbon, PT, 9 pages, Oct. 4-6, 2012.
Navarro De Lara, Lucia Isabel, et al, A Novel High Sensitivity MR-Device for Combined TMS/fMRI Experiments, 5th International Conference on Non-Invasive Brain Stimulation, Leipzig, G, NBS, Mar. 19-21, 2013.
Navarro De Lara, Lucia Isabel, et al, A New MR Device for Combined TMS/fMRI Experiments, Organization for Human Brain Mapping, Seattle, WA, USA, 4 pages, Jun. 16-20, 2013.

* cited by examiner

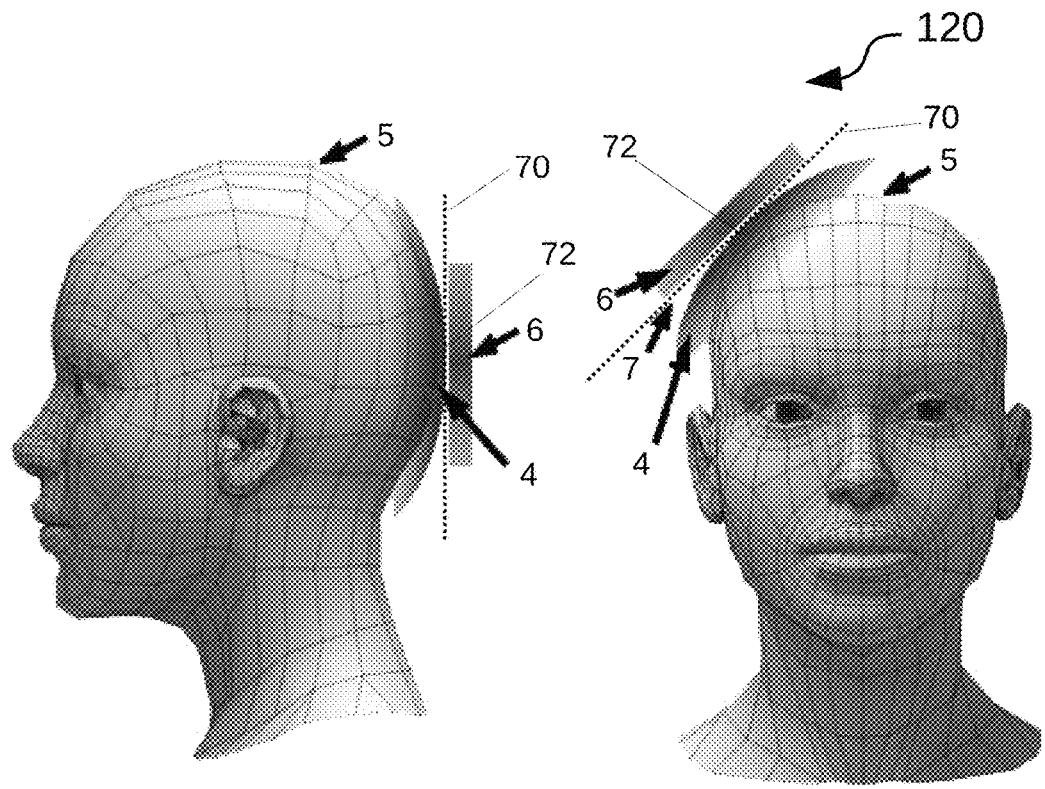
*FIGURE 3A*  *FIGURE 3B*
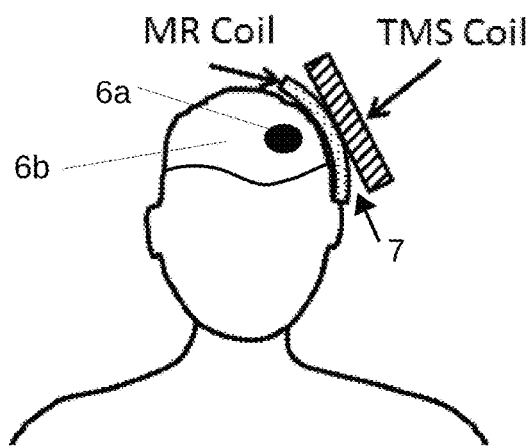
*FIGURE 3C*

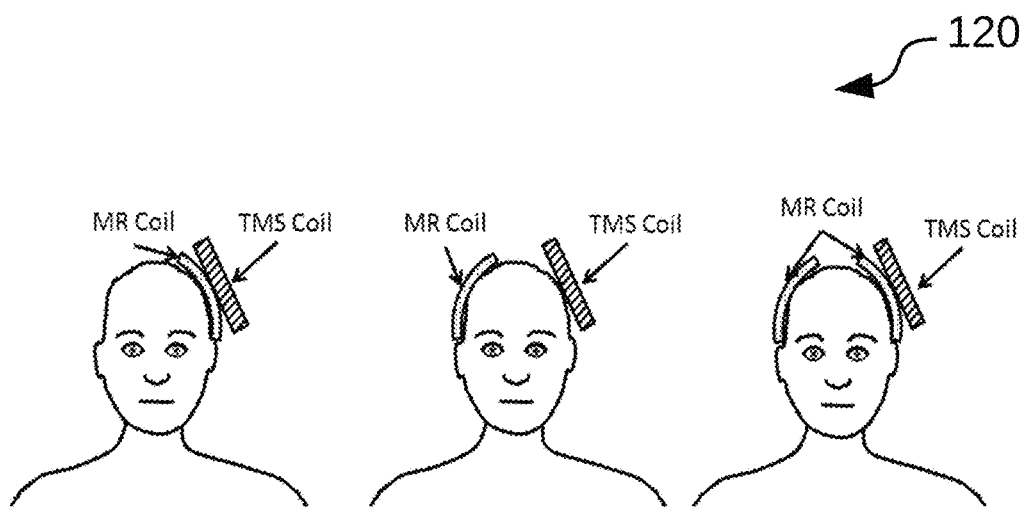
*FIGURE 14A*  *FIGURE 14B*  *FIGURE 14C*
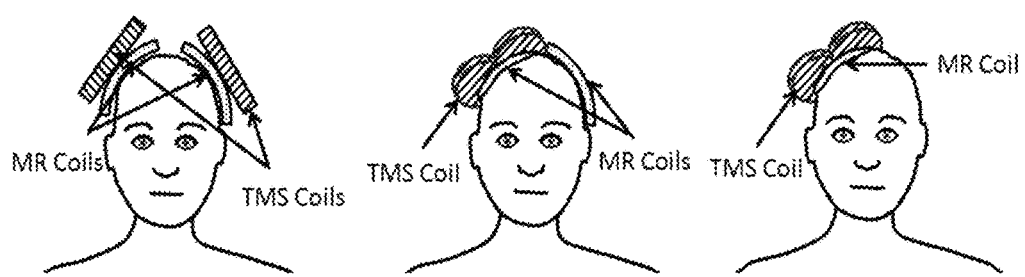
*FIGURE 14D*  *FIGURE 14E*  *FIGURE 14F*

METHOD AND SYSTEM FOR COMBINED TRANSCRANIAL MAGNETIC SIMULATION (TMS) AND FUNCTIONAL MAGNETIC RESONANCE IMAGING (FMRI) STUDIES

FIELD OF THE INVENTION

The present invention generally relates to the field of magnetic stimulation of neurons and magnetic resonance imaging, and in particular, to a method and system for combined transcranial magnetic stimulation (TMS) and a functional magnetic resonance imaging (fMRI) studies.

BACKGROUND OF THE INVENTION

For the last fifteen years, transcranial magnetic stimulation combined with functional magnetic resonance imaging studies has firmly established its reputation as a leading non-invasive technique for medical/neurological studies, diagnostic tool and even as a therapeutic device for many medical/neurological and psychiatric conditions, especially in the treatment of certain types of depression.

In a typical prior art arrangement, shown on FIGS. 1 and 2, a TMS coil 1 is positioned next to a scalp 2 of a patient over an area of neurological interest, for example, a part of the brain cortex, so that the stimulation area of neurological interest is within an operational reach of the TMS coil 1. A pulsed magnetic field from the TMS coil 1 induces an electric current in the part of the brain cortex, locally depolarizing its neurons. This stimulates a response from the local neurons, and oftentimes even neurons that are far away from the stimulation area of neurological interest. The response from the neurons may result in subtle changes in a blood oxygenation level in the affected areas, from which brain cortex activity can be inferred. Since the blood oxygenation level can be visualized using fMRI techniques, the visualization effectively amounts to the visualization of brain cortex activity, though indirectly.

For the purpose of visualization, the head of the patient is subjected to a strong static magnetic field, which causes polarization of the nuclear spins in the body. Electromagnetic radiation with a frequency equal to the Larmor frequency of the nucleus of interest, usually hydrogen nuclei (i.e. protons), further referred to as a MR transmit pulse, excites the selected spin system to a higher energy level, and causes the protons to precess around the direction of the static magnetic field, thus, emitting a weak electromagnetic radiation. We will further refer to the weak response of protons as the MR signal.

The MR signal is picked up by an MR receiver coil 3, positioned further away from the TMS coil 1 and the scalp 2 of the patient. The MR receiver coil 3 will be further referred to simply as an MR coil. After appropriate, and often sophisticated, computer processing of the MR signal, an image of the affected area of the brain cortex is formed. More detailed description of the TMS and fMRI can be found, for example, in U.S. Pat. No. 5,732,702 to Edgar Mueller entitled "Method and apparatus for functional imaging" issued on Mar. 31, 1998.

Although the above arrangement for combined TMS/fMRI studies has served the researchers reasonably well in the past, its shortcomings are quickly becoming a limiting factor in meeting new research and application demands.

A problem that requires particular attention of engineers is the low signal-to-noise ratio (SNR), which, in part, is caused by the weak MR signal, but also due to the fact that MR coils in previous combined TMS/fMRI studies had to be large enough to accommodate both, the head and the TMS coil. This required large sized MR coils having a large distance to the head, thereby reducing the achievable SNR.

Since increasing the MR signal itself does not seem to be feasible, because of physical limitations of the MR process, prior art offers various solutions, such as accumulation and subsequent statistical processing of the MR signal using sophisticated algorithms.

Unfortunately, the solutions offered by the prior art have been only partially successful, and have often introduced new problems, which are sometimes difficult to solve. For instance, the accumulation of the weak MR signal requires long measurement time, which may cause discomfort to a patient or be outright impossible for visualization of relatively fast dynamic processes, such as heartbeat etc.

Therefore, there is a need in the industry for further development of an improved TMS/fMRI system and method, which would provide further improvements to the TMS/fMRI studies, and avoid or mitigate the above noted problems of the prior art.

SUMMARY OF THE INVENTION

Accordingly, there is an object of the invention to provide an improved method and system for combined TMS/fMRI studies which would avoid or mitigate the shortcomings of the prior art.

There is another object of the invention to provide an improved method and system for combined TMS/fMRI studies, which would provide higher SNR and faster processing of MR signals than existing prior art techniques.

There is another object of the invention to provide an improved MR coil for MRI studies, which would also be suitable for use in the combined TMS/fMRI studies.

According to one aspect of the invention, there is provided a system for combined transcranial magnetic stimulation (TMS) and functional magnetic resonance imaging (fMRI) studies, comprising:

a TMS coil for stimulating a stimulation area;
a coil for magnetic resonance imaging, an MR coil, for MR imaging of the stimulation area and an area surrounding the stimulation area;
the TMS coil and the MR coil being spatially arranged to allow said stimulating to be performed through the MR coil.

The system further comprises a means for preventing motion of the TMS coil with respect to the MR coil caused by a magnetic field generated by the TMS coil.

In the system described above, the thickness of the MR coil in the stimulation area is such to ensure that the stimulation area is within an operational reach of the TMS coil.

In an embodiment of the invention, the thickness of the MR coil has been in a range of 5-7 mm, however it is understood that the MR coil may be thinner or thicker as long as the stimulation area for TMS is within the operational reach of the TMS coil.

Beneficially, the MR coil has a shape substantially corresponding to the shape of an object of medical studies, for example neurological studies, to which the TMS is to be applied.

For example, the MR coil may have the shape of a cap suitable for fitting onto a human head. Conveniently, the shape of the cap may be one of the following: a spherical cap, an elliptical cap, a parabolic cap, a hyperbolic cap, a cylindrical cap or another shape cap fitting the shape of the head. Other parts of a human body may be examined similarly, by using an appropriate shape of the MR coil.

In the system described above, the MR coil further comprises electronic components for operating the MR coil; and those electronic components, which are responsible for controlling an operation of the MR coil in the stimulation area, are disposed outside the stimulation area between the cap and a tangent plane at a tip.

The system as described above, wherein the means for preventing motion comprises a base for holding an MR coil; and the shape of the base closely resembles the shape of said object.

In the system described above, the means for preventing motion comprises a fixing means for fixing the TMS coil and the MR coil together as an integral unit. It is understood that various kinds of fixing means can be used as long as they prevent motion of the TMS with respect to the MR coil during operation.

In the embodiments of the invention, the MR coil is a phased array coil, comprising two or more basic elements for processing radio frequency signals generated during the fMRI; and two or more assemblies of electronic components for respectively operating said two or more basic elements.

To minimize the thickness of the MR coil in the stimulation area, an assembly of electronic components, associated with a basic element in the stimulation area, is disposed outside of the stimulation area.

Remaining assemblies of electronic components, associated with those basic elements, which are outside the stimulation area, may be disposed either inside respective basic elements, or outside respective basic elements.

Further, to suppress the antenna effect in the basic elements, the basic elements of the MR coil are divided into two or more sections having section ends, which are connected electrically and mechanically by one or more capacitors, placed between respective section ends. To minimize the thickness of the MR coil, these capacitors have been removed from the electronic assemblies and embodied directly into the basic elements.

In the embodiments of the invention, an assembly of electronic components associated with a basic element in the stimulation area, comprises a printed circuit board, and a planar inductor for detuning said basic element, the planar inductor being electrically connected to the printed circuit board, and disposed outside of the printed circuit board substantially in the same plane as the printed circuit board.

To study the response, caused by TMS, by the MRI techniques, basic elements, other than those basic elements in the stimulation area, are arranged to cover a surrounding area around said stimulation area.

In the embodiments of the invention, the MR coil comprises seven basic elements, six of which are arranged substantially according to a hexagonal structure, with the remaining seventh basic element being placed substantially in the middle of the hexagonal structure to substantially correspond to the stimulation area.

According to yet another aspect of the invention, there is provided a method for combined transcranial magnetic stimulation (TMS) and functional magnetic resonance imaging (fMRI) studies, the method comprising:
  stimulating a stimulation area by a TMS coil, and performing fMRI of the stimulation area and an area surrounding the stimulation area by an MR coil, comprising:
  spatially arranging the TMS coil and the MR coil so as to allow said TMS stimulating to be performed through the MR coil.

The method further comprises preventing motion of the TMS coil with respect to the MR coil caused by a magnetic field generated by the TMS coil.

The method further comprises shaping the MR coil in a form of a cap; and positioning the TMS coil in proximity of a tip of the cap.

According to yet another aspect of the invention, there is provided a coil for magnetic resonance (MR) imaging, an MR coil, comprising:
  two or more basic elements for processing radio frequency signals generated during the magnetic resonance imaging;
  the thickness of the MR coil in an area occupied by at least one basic element is such that to allow for operation of a transcranial magnetic stimulation (TMS) coil through the MR coil in said area for combined TMS and functional magnetic resonance imaging (fMRI) studies.

The coil further comprises means for preventing motion of the MR coil, relative to the TMS coil, caused by a magnetic field generated by the TMS coil.

In the embodiments of the invention, the MR coil has the shape of a cap, and said area is centered around the tip of the cap.

The MR coil described above, wherein the means for preventing motion comprises a fixing means for fixing the TMS coil and the MR coil together as an integral unit.

For example, the MR coil may have the shape of a cap, which is one of the following: a spherical cap, an elliptical cap, a parabolic cap, a hyperbolic cap, a cylindrical cap or another shape cap fitting the shape of the head.

Generally, the MR coil has a shape substantially corresponding to the shape of an object of medical studies, e.g. neurological studies, to which the TMS is to be applied.

In the MR coil described above, at least one basic loop element is undivided or is divided into two or more sections having section ends, which are connected electrically and mechanically by one or more capacitors, placed between respective section ends, said one or more capacitors being used for suppressing antenna effect in the basic loop elements.

Alternatively, within the MR coil, as described above, to suppress the antenna effect in the basic elements, the basic elements of the MR coil are divided into two or more sections having section ends, which are connected electrically and mechanically by one or more capacitors, placed between respective section ends. To minimize the thickness of the MR coil, these capacitors have been removed from the electronic assemblies and embodied directly into the basic elements.

The MR coil, as described above, further comprises two or more assemblies of electronic components for respectively operating the two or more basic elements, an assembly of electronic components associated with said at least one basic element being disposed outside said area for TMS.

In the MR coil described above, assemblies of electronic components associated with basic elements, other than said at least one basic element, may be disposed inside respective basic elements. Alternatively, they may be disposed outside respective basic elements.

In the MR coil described above, the means for preventing motion comprises a base for holding an MR coil; and the shape of the base closely resembles the shape of a cap.

The MR coil further comprises two or more assemblies of electronic components for operating the two or more respective basic elements, an assembly of electronic components associated with said at least one basic element being disposed outside said area between the cap and a tangent plane to the cap at the tip.

In the embodiments of the invention, the electronic components associated with said at least one basic element, comprise a printed circuit board, and a planar inductor for detuning said at least one basic element, the planar inductor being electrically connected to the printed circuit board, and disposed outside of the printed circuit board substantially in the same plane as the printed circuit board.

Conveniently, the basic elements of the MR coil, other than said at least one basic element, are arranged to cover a surrounding area around said at least one basic element.

The MR coil of the embodiment of the invention comprises seven basic elements, six of which are substantially arranged according to a hexagonal structure, with the remaining seventh basic element being placed substantially in the middle of the hexagonal structure; the seventh basic element being said at least one basic element through which the TMS is applied.

Thus, an improved method and system for combined TMS/fMRI studies, as well as an improved MR coil for MRI and combined TMS/fMRI studies, have been provided.

BRIEF DESCRIPTION OF THE DRAWINGS

Embodiments of the invention will now be described, by way of example, with reference to the accompanying drawings, in which:

FIG. 3A shows a mutual spatial arrangement of the TMS coil 6 and the MR coil 4 of the embodiments of the present invention positioned against an occipital bone of a head 5;

FIG. 3B shows a mutual spatial arrangement of the TMS coil 6 and the MR coil 4 of the embodiments of the present invention positioned at an angle against a parietal bone of a head 5;

FIG. 3C illustrates a stimulation area and an area surrounding the stimulation area;

FIG. 14A shows a spatial arrangement of the TMS coil and the MR coil, where the MR coil is placed between the head and the TMS coil;

FIG. 14B shows a spatial arrangement of the TMS coil and the MR coil, where the MR coil and TMS coil are placed at different positions on the head;

FIG. 14C shows a spatial arrangement of the TMS coil and the MR coil of FIG. 14A, with yet an additional MR coil placed at a different position on the head;

FIG. 14D shows two TMS/fMRI systems of FIG. 14A, placed on different sides of the head, for double stimulation;

FIG. 14E shows the spatial arrangement of the TMS coil and the MR coil of FIG. 14C, placed on a different area of the head; and FIG. 14F shows the spatial arrangement of the TMS coil and the MR coil of FIG. 14A, placed on a different area of the head.

DETAILED DESCRIPTION OF THE EMBODIMENTS OF THE INVENTION

Figure 1:
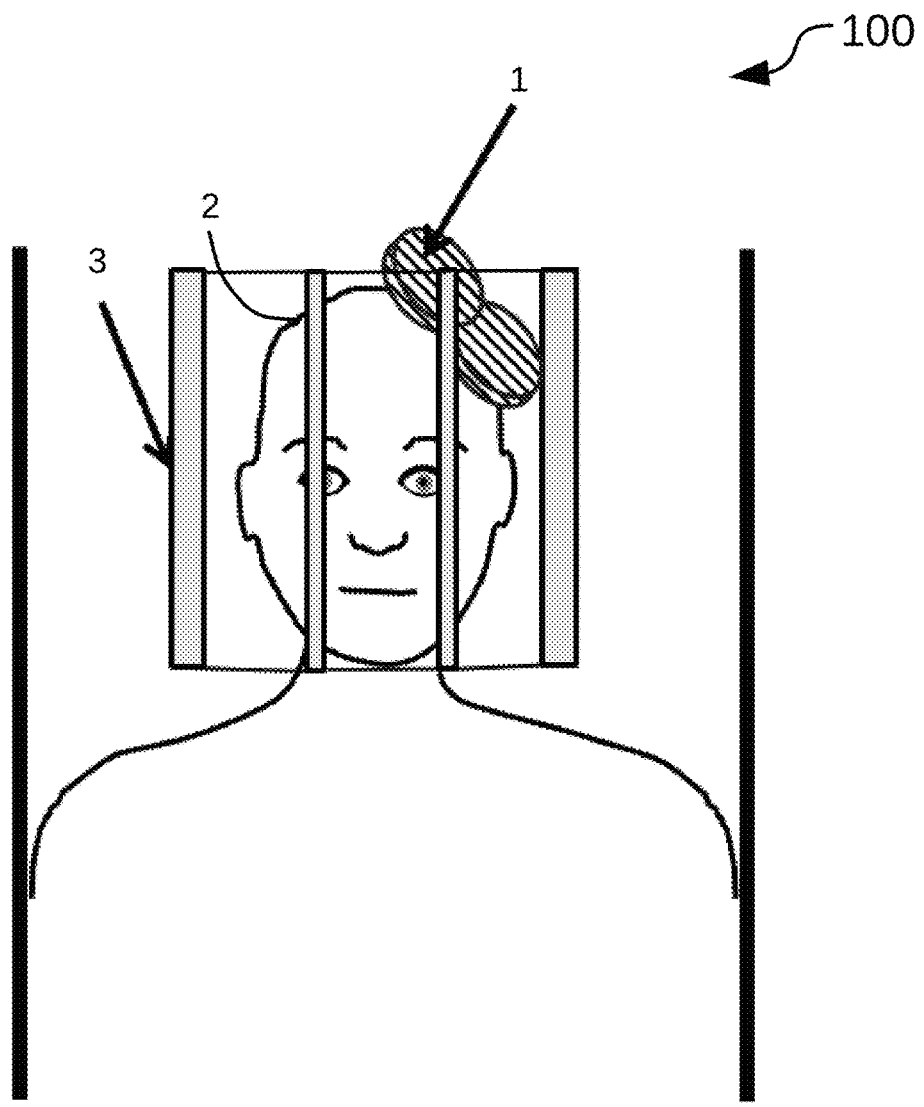
FIG. 1 schematically illustrates a prior art system for combined TMS/fMRI studies.
Figure 2:
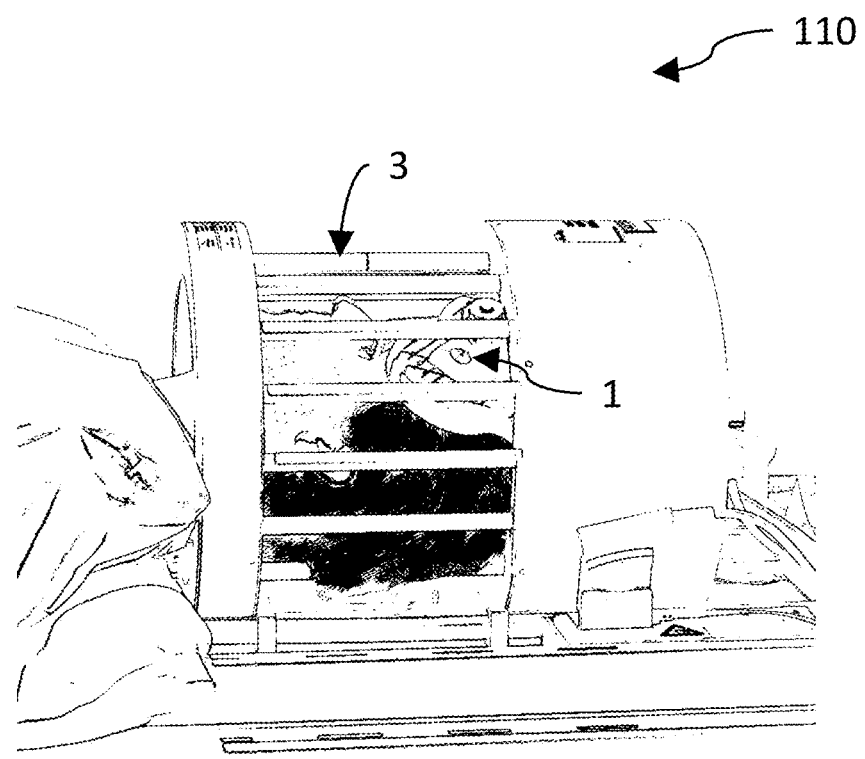
FIG. 2 shows a commercial implementation of the prior art system of FIG. 1.

The embodiments of the present invention provides the improved TMS/fMRI system with better SNR due to a special spatial arrangement of the TMS coil and the MR coil, where the TMS is performed through the MR coil, which is positioned in a sandwich arrangement between the TMS coil and a head of a patient (or another organ of a body to be studied).

A system 120 for combined TMS/fMRI studies of an embodiment of the invention is illustrated in FIGS. 3A and 3B. In particular, FIG. 3A shows a mutual spatial arrangement of the TMS coil 6 and the MR coil 4 positioned against an occipital bone of a head 5; and FIG. 3B shows a mutual spatial arrangement of the TMS coil 6 and the MR coil 4 positioned at an angle against a parietal bone of the head 5.

An MR coil 4 is placed between the head (scalp) 5 of a patient and the TMS coil 6, in a "sandwich" arrangement, and the TMS coil 6 provides stimulation to the stimulation area 6a of neurological interest (further referred to as stimulation area 6a) in the brain cortex through the MR coil 4.

The MR coil 4 is centered on the head (scalp) 5 of the patient somewhere above the stimulation area 6a, and also covers an area 6b surrounding the stimulation area (not shown in FIG. 3), providing a field of view from 10 cm to 25 cm, and the target depth for brain cortex studies between 3 cm and 10 cm.

The TMS coil 6, being a substantially planar object, is placed so that it is substantially parallel to the tangent plane 70 to the spherical cap at its tip 72, as shown in FIGS. 3A and 3B.

FIG. 3C schematically illustrates the stimulation area 6a and the area 6b surrounding the stimulation area.

In the embodiments of the invention, an MR coil 4 is a phased array coil, or a multichannel surface head coil, which has a high sensitivity and allows for implementing parallel imaging, which has potential to speed up the data acquisition during the TMS/fMRI process considerably.

Figure 4:
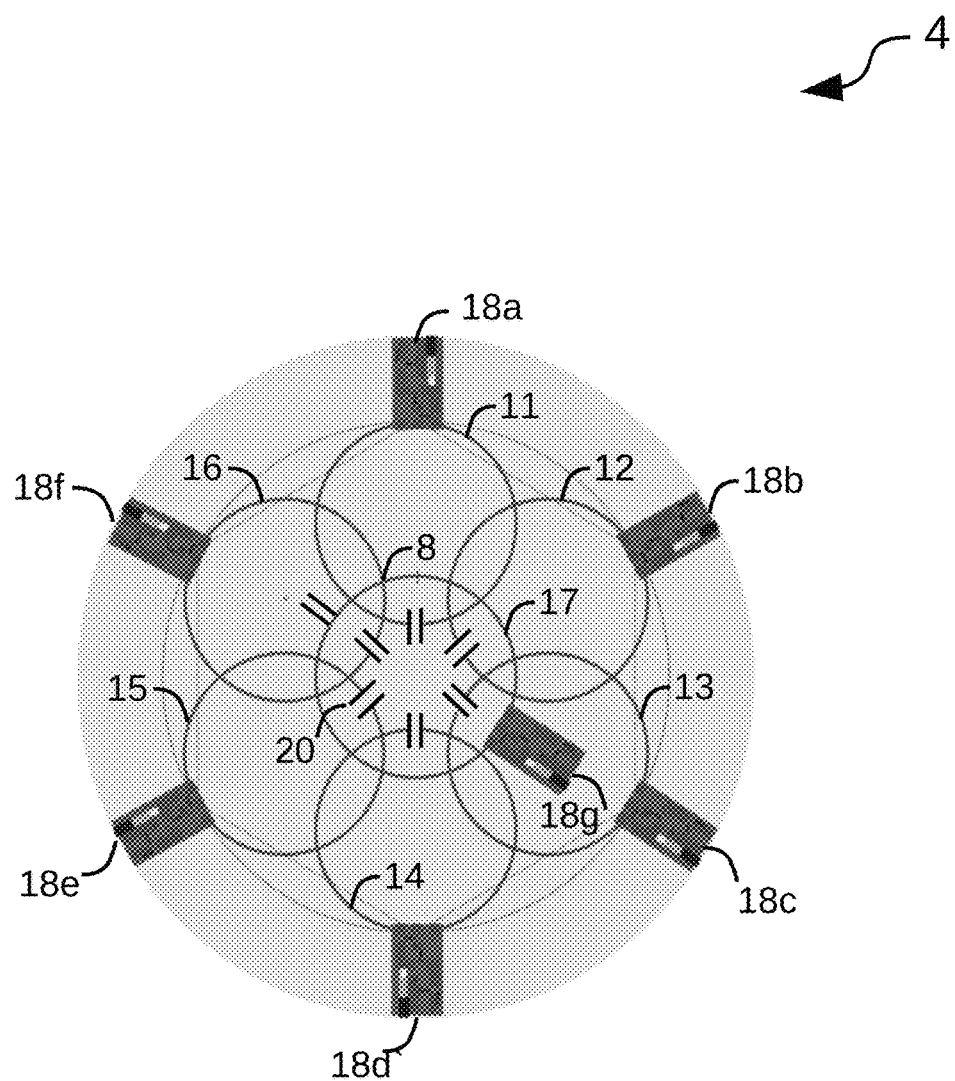
FIG. 4 is a schematic illustration of the design of the ultra-thin MR coil 4 of one embodiment of the present invention.

Specifically, the MR coil 4 of the embodiments of the invention, shown schematically on FIG. 4, has been designed to include seven basic elements 11-17, each having a diameter of about 6 cm.

Six basic elements 11-16 are arranged into a substantially hexagonal structure, i.e. the structure, in which segments of a straight line, connecting centers of said basic elements, create a figure resembling a hexagon. The seventh basic element 17 is placed substantially in the middle of the hexagonal structure.

Each basic element 11-16 partially overlaps with the central basic element 17 and partially overlaps (or is overlapped by) two of its neighbors. The basic elements 11-17 are made from insulated copper wire of 1.5 mm in diameter. Mechanical contacts between overlapping parts of the basic elements have been avoided by bending the top wires at the points of contact 8 (for clarity, only one point of contact 8 is provided with the reference numeral). Said bending is shown in more detail on FIG. 5.

In the embodiments of the invention, the TMS coil 6 is positioned substantially against the central basic element 17 such that the stimulation area 6a is somewhere in the brain beneath the central loop element 17, while the area 6b surrounding the stimulation area is located outside and around the central basic element 17, for example, somewhere in the brain beneath the other basic elements 11-16. Thus, the MR coil 4 provides imaging of the stimulation area 6a and the area 6b surrounding the stimulation area.

Each basic element has been cut into two sections so that the length of each section is smaller than $\lambda/10$, where $\lambda$ is the wavelength of the MR signal. The two sections have been connected by an MR compatible ceramic chip capacitor 20, such as commercially available from TEMEX CERAMICS Corporation of Pessac, France. For simplicity, only one capacitor has been labeled with the reference numeral 20 in FIG. 4.

The capacitor 20 serves the purpose of minimizing the "antenna effect" in the basic elements by keeping the length of each segment of wire short as compared to the wavelength of the radio frequency signal.

FIG. 4 also shows seven printed circuit boards (PCBs) 18a-18g associated with the respective basic elements 11-17, the PCBs 18a-18g to be described in more detail with regard to FIG. 6 below.

Figure 5:
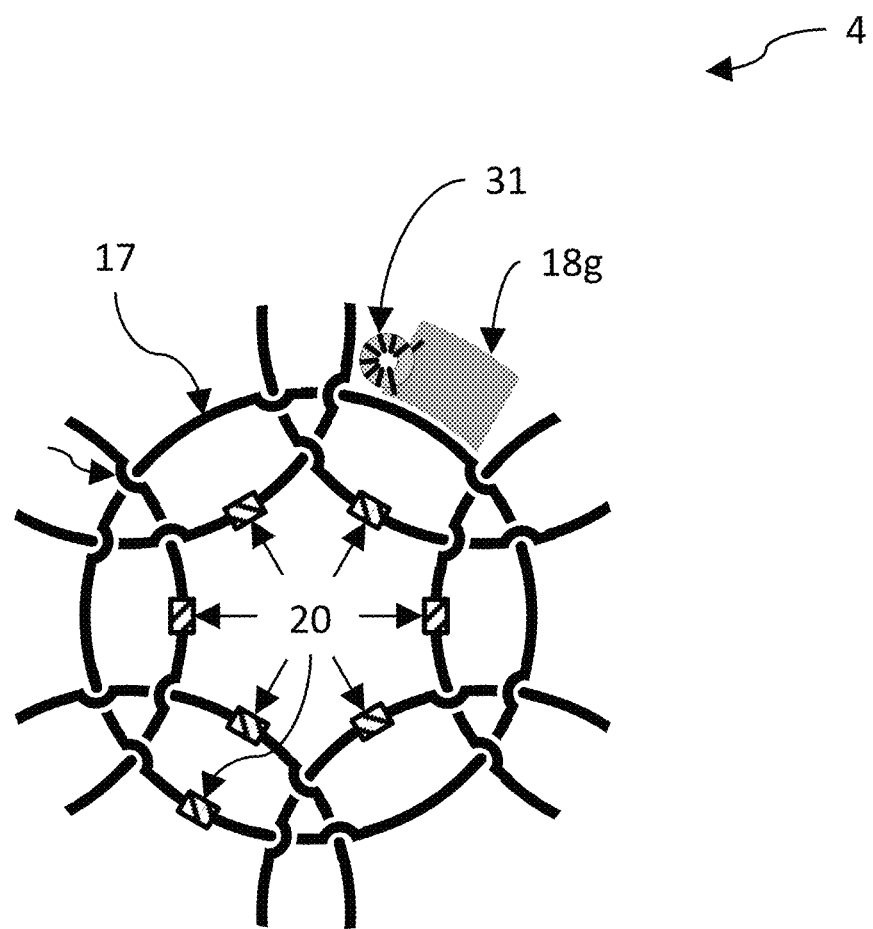
FIG. 5 shows a central part of the MR coil of FIG. 4 in more detail, including a basic element 17.

FIG. 5 shows a central part of the MR coil of FIG. 4 in more detail, including the basic element 17 and capacitors 20 connecting two respective sections of other basic elements. It can be seen that the capacitor 20 has been soldered to the respective ends of said two sections, which provides both the required electrical and mechanical connection.

For the purpose of MR signal acquisition and MR signal processing, a basic element may be referred to as a channel, therefore the MR coil 4 of the preferred embodiment may be referred to as a 7-channel phased array 4.

It is understood that for larger basic elements, each of the basic elements may be divided into two or more sections having section ends, which are connected electrically and mechanically by one or more capacitors, placed between respective section ends, the one or more capacitors being used for suppressing the antenna effect in the basic element.

As mentioned above, the basic elements 11-17 are provided with respective assemblies of electronic components required for its operation, each comprising a printed circuit board (PCB) 18a-18g, and a cable 32 connecting each PCB to a respective preamplifier 24 (shown in FIG. 6) housed in a separate interface box 22 containing the preamplifiers for all basic elements. PCBs for basic elements 11-17 have been labeled 18a-18g respectively as shown in FIG. 4, and also all PCBs will be referred to as PCBs collectively. FIG. 5 shows a partial view of the PCB 18g associated with the basic element 17, with an arrow pointing out at one of the inductors located at the PCB 18g, namely the inductor 30 as will be described in more detail with regard to FIG. 6.

Each PCB 18a-18g contains electronic components for creating optimal conditions for acquiring the MR signal, and for detuning the entire MR coil 4 during the generation of MR transmit pulses.

Figure 6:
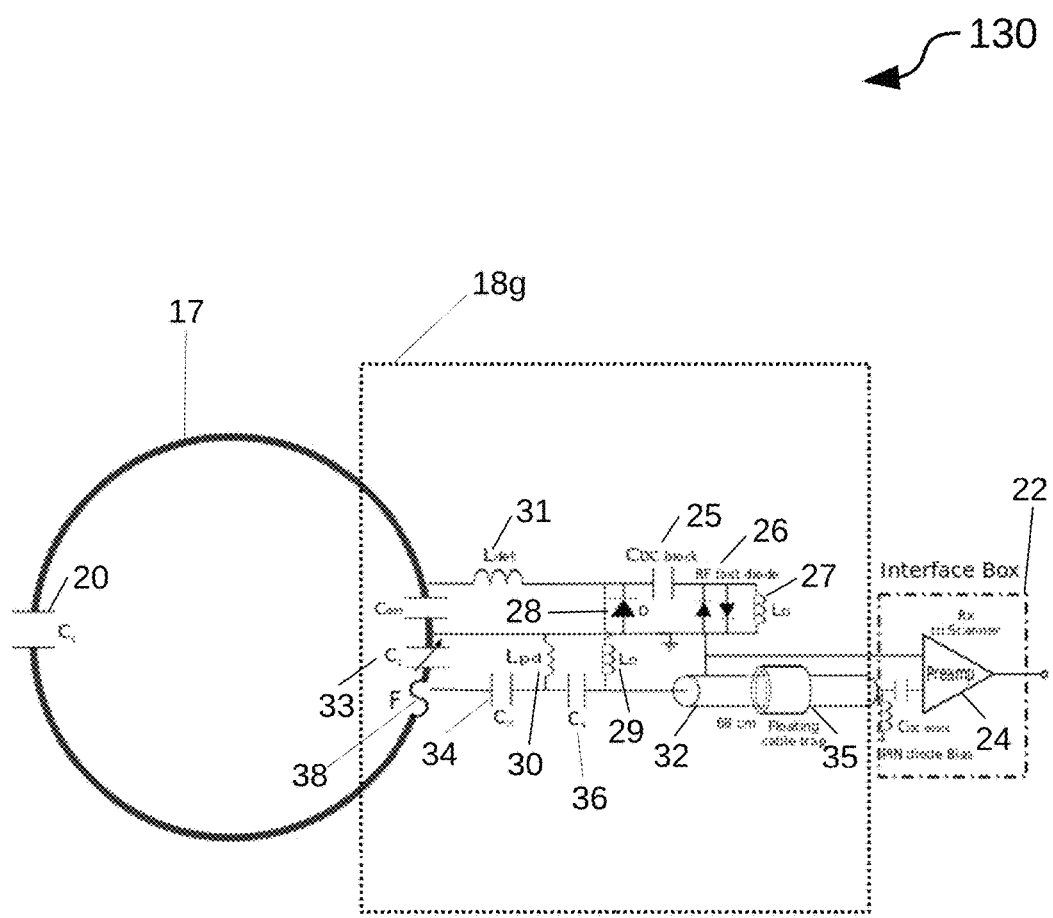
FIG. 6 shows a circuit diagram for electronic components for basic elements of the ultra-thin MR coil 4 of the embodiments of the invention.

A combined circuit diagram 130 for one of the PCBs 18, the Interface box 22 and one of the basic elements is shown on FIG. 6, where the basic element 17 and PCB 18g have been shown just for example.

In the embodiment of the invention, where the TMS coil 6 is placed on top of the MR coil 4, a strong pulsating magnetic field of about 2 T, generated by the TMS coil 6 in its immediate vicinity, may induce high currents in the basic elements 11-17 of the MR coil 4. These high currents may burn preamplifiers 24 and may raise the temperature of the MR coil 4 to a dangerous to a patient level, which is unacceptable.

Each basic element 11-17 is tuned to the Larmor frequency of $^1$H (123, 25 MHz for 3 Tesla MR systems) and the MR coil 4 has a very high impedance in the range of frequencies characteristic for the TMS coil 6 (several KHz). As a result, the TMS coil 6 induces very low currents in the MR coil 4 of about 5 microampere only, which are harmless for both the preamplifiers and the patient.

Each basic element is matched to about 50Ω, for which the preamplifiers present the lowest level of noise (noise matching).

The PCBs 18 also provide for a system of triple protection against high currents, which could be induced in the basic elements during generation of the MR transmit pulses required for normal operation of fMRI.

The first level of protection is provided by fuses 38 shown in FIG. 6, normally operated at a nominal current rating of about 750 mA.

The second level of protection is provided by a passive detuning system, which includes of a DC-Block capacitor 25, RF fast diodes 26 and an inductor 27 to short the switching currents, thereby minimizing noise created by the fast diodes 26 with small DC currents. The DC-Block capacitor 25, such as one of the 122CPX102G series of RF power capacitors, is commercially available from TEMEX Ceramics Corporation (now Rakon France SAS), Pessac, France. The fast RF diodes 26, such as UM9989, are commercially available from Microsemi Corporation, Aliso Viejo, Calif., USA. The inductor 27, such as 1812 CS, is commercially available from Coilcraft, Inc., Cumbernauld, Scotland.

The third level of protection is provided by an active detuning system including a PIN diode 28, such as DH 80106, which is commercially available from TEMEX Ceramics corporation (now Rakon France SAS), Pessac, France. The PIN diode 28 is biased through an RF choking coil 29, such as 1812 CS, which is commercially available from Coilcraft, Inc., Cumbernauld, Scotland.

In order to minimize high coupling between non-adjacent basic elements 11-17, preamplifier decoupling is implemented for each basic element. For this purpose, a second order matching network, comprising capacitor C2 (33), capacitor C3 (34), inductor $L_{pd}$ (30), and capacitor C4 (36), proposed for example by Reykowski, has been designed for each basic element, see Reykowski, A., Wright, S. M., & Porter, J. R., 1995, "Design of matching networks for low noise preamplifiers", *Magnetic Resonance in Medicine,* 33, 848-852.

The proposed structure A-2 of second order matching network of Reykowski has been selected to minimize possible coupling between the inductor 30 used to achieve preamplifier decoupling and the inductor 31 used to detune the MR coil 4 during generation of the MR transmit pulses.

Preamplifiers 24, such as those commercially available from Siemens Healthcare AG, Erlangen, Germany, are not placed directly on the MR coil 4 for two main reasons. Firstly, it is advisable to keep the preamplifier 24 as far as possible from the TMS coil 6 to avoid subjecting the preamplifiers 24 to a rather strong magnetic field (~2 T) generated by the TMS coil 6 during its operation. Secondly, said preamplifiers 24 are rather bulky devices and considerably increase the thickness of the MR coil 6. Therefore, a coaxial cable 32, such as K-02252-D from Huber+Suhner corporation, Herisau, Switzerland, with a length of about 68 cm has been used to keep the preamplifiers 24 away from the MR coil. Input impedance of the preamplifiers 24 with the coaxial cable 32 is almost like a short circuit (~1Ω). The second order matching network transforms the short circuit to an open circuit at the output (not shown) of each basic element 11-17, thereby minimizing the crosstalk between channels (between basic elements 11-17).

For the fine tuning of the MR coil 4, variable capacitors 33, such as TZC3 from Murata corporation, Kyoto, Japan, have been built as part of the second order matching network. The preamplifiers 24 have been placed in an interface box 22. The preamplifiers 24 also contain a bias-T for the PIN diode 28, which makes it possible to apply the required bias to the PIN 28 diode on each basic element 11-17, to detune the basic elements 11-17 during generation of the MR transmit pulses.

In order to suppress common mode currents, floating cable traps 35 have been placed on each cable connecting each basic element 11-17 to its respective preamplifier 24. Floating cable traps 35 have also been placed on the output cables of the preamplifiers 24 to the scanner (not shown). The floating cable traps have been designed as described for example in Seeber, D. a., Jevtic, J., & Menon, A., 2004, "Floating shield current suppression trap", *Concepts in Magnetic Resonance Part B: Magnetic Resonance Engineering,* 21B(1), 26-31. doi:10.1002/cmr.b.20008.

Figure 7:
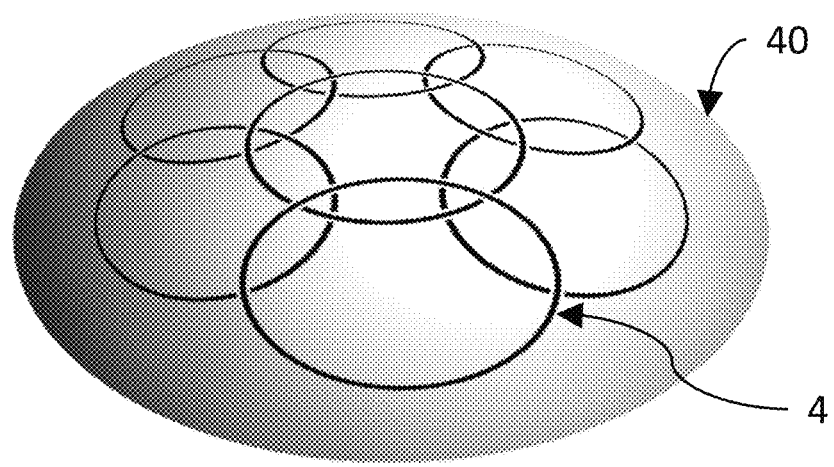
FIG. 7 shows the ultra-thin MR coil 4 of FIG. 4 placed on a plastic base.

For mechanical stability, the MR coil 4 has been placed on a 3 mm thin plastic base 40 as shown in FIG. 7.

In the embodiments of the present invention, the choice of the shape of the base has been dictated by the natural curvature of the objects for neurological studies and clinical practice, such as the head of a human being, knees etc. Therefore, the MR coil 4 has a shape substantially corresponding to a shape of an object of neurological studies, to which the TMS is to be applied, e.g. the shape of a cap suitable for fitting onto a human head.

It has been found that shaping the plastic base 40 as a spherical cap of a suitable diameter, e.g. about 22 cm for brain cortex studies, or generally between 15 cm to 30 cm, provides for several benefits, such as more uniform SNR for each basic element due to substantially similar distance between each basic element of the MR coil 4 and a part of the body being studied. However, in other embodiments, a different shape of the plastic base 40, for example an elliptical cap, a parabolic cap, a hyperbolic cap, a cylindrical cap etc., may be also used.

As mentioned above with regard to FIGS. 3A and 3B, the TMS coil 6, being a substantially planar object, is placed so that it is substantially parallel to the tangent plane 70 to the spherical cap at its tip 72. The center of the TMS coil 6 substantially coincides with the center of the central basic element 17 of the MR coil 4. However, in other embodiments, a different positioning of the center of the TMS coil 6, and a different orientation of the TMS coil 6 may be advantageous.

During operation, the TMS coil 6 creates a strong magnetic field of about 2 T in its immediate vicinity. This magnetic field rapidly decays away from the TMS coil 6, so that even in the center of the basic element 17, where it is the strongest, a typical operational reach of the TMS coil 6 (i.e. a distance from the TMS coil 6 to the stimulation area 6a) is about 2-4 cm in depth. Therefore, to perform its intended function, the TMS coil 6 should not be positioned too far away from the head (scalp) 5 of a patient. In practice, the distance to the head (scalp) 5 of the patient should be as small as possible, much smaller than 2 cm and preferably in the range of 0-10 mm.

In the embodiments of the invention, the minimal distance from the TMS coil 6 to the head (scalp) 5 of the patient is determined by the thickness of the MR coil 4.

For this reason, the present invention provides for a novel ultra-thin design of the MR coil 4 having thickness in a range of 2 mm or 3 mm-10 mm, which is especially suitable for concurrent use with the TMS coil in the TMS/fMRI system of the present invention. The thickness of the MR coil 4 of the embodiments of the invention is smaller than 2 cm, for example, smaller than 15 mm, or smaller than 12 mm, preferably smaller than 10 mm, and more preferably smaller than 7 mm, and yet preferably smaller than 5 mm, for example in a range of a fraction of a millimeter to 10 mm.

Figure 8:
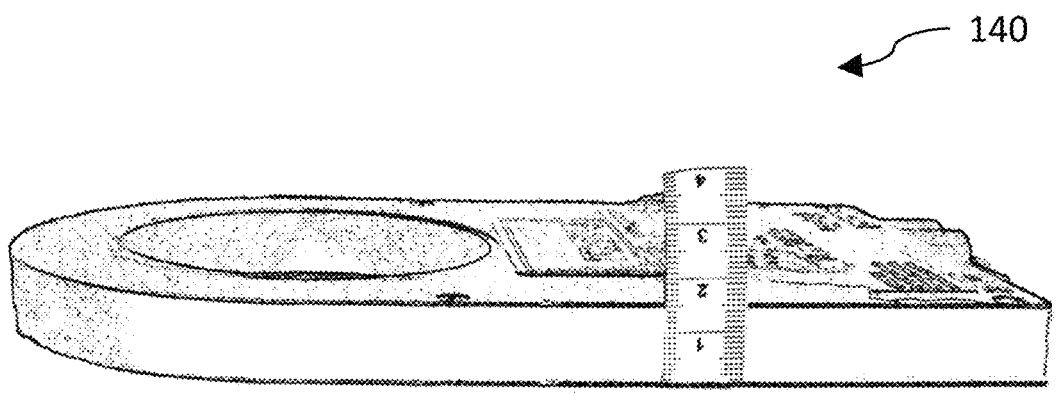
FIG. 8 shows a prior art MR coil packaged in a housing.

For comparison, FIG. 8 shows an existing prior art MR coil 140 manufactured by Siemens AG, Germany, having a thickness in excess of 1.5 cm.

The most bulky components of a traditional prior art MR coil that largely determine the overall thickness of the MR coil are its PCBs 18, containing electronic components on the PCBs 18. It has been determined that the most offending in terms of increasing the PCB's thickness are two components of the PCB—the capacitor 20 and the inductor 31.

The capacitor 20 is normally mounted on a pad (not shown), which contributes to the thickness of the MR coil 4. It has been decided to remove the pad, and to solder the capacitor 20 directly to the ends of the sections of a corresponding basic element (11-17), as shown on FIGS. 4 and 5.

Figure 9:
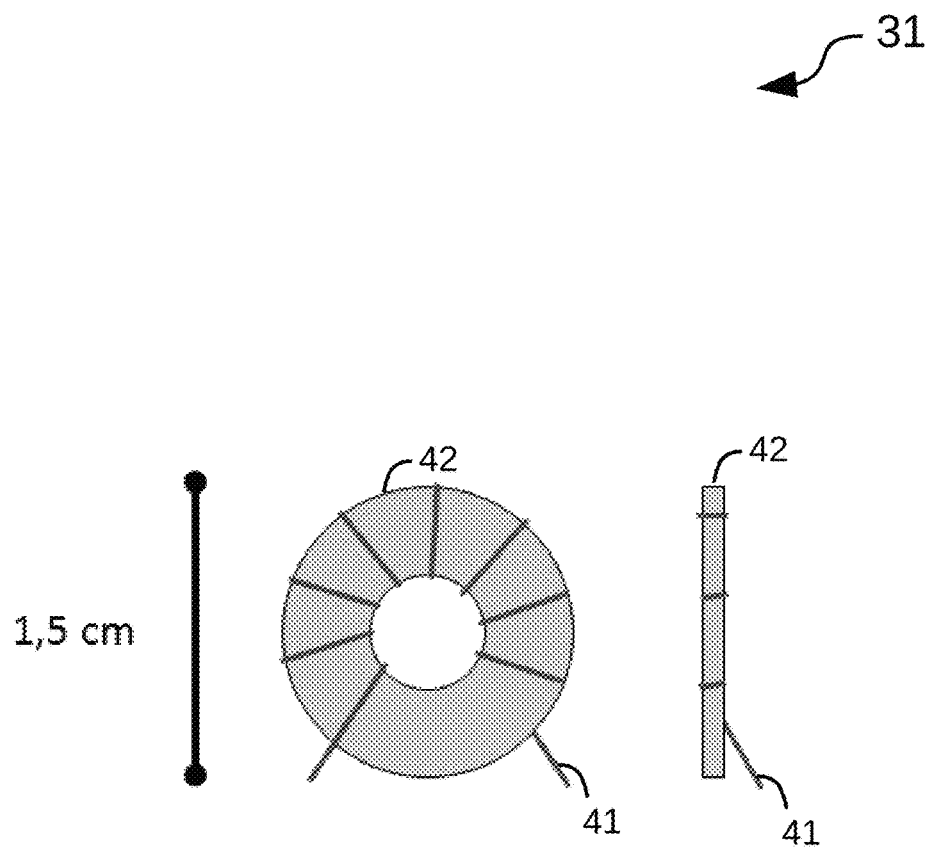
FIGS. 9A and 9B respectively illustrate a front view and a side view of a custom designed inductor for the ultra-thin MR coil 4 of the embodiments of the invention.

FIGS. 9A and 9B respectively illustrate a front view and a side view of a custom designed inductor 31 for the ultra-thin MR coil 4 of the embodiments of the invention. The inductor 31 has a plastic insert 42 and a copper wire 41 of 0.5 mm in diameter, which is wound into a coil around the plastic insert 42. The ends of the wire 41 have been connected to corresponding contacts on the PCB 18 (for example PCB 18g shown in FIG. 6), but the body of the inductor has been positioned next to the PCB 18 in such a way that the plastic insert 42 and the PCB 18 are substantially coplanar with each other. A relative positioning of the inductor and the PCB 18g are illustrated on FIG. 5. With these modifications, the thickness of the PCB 18g has been reduced to about 3 mm. We will further refer to the new, slimmer PCB 18g as a planar PCB 18g. It is understood that other PCBs 18a-18f can be also made similar to the PCN 18g as described above.

Thus, the assembly of electronic components, associated with a central basic element 17 in the stimulation area, comprises a printed circuit board 18g, and a planar inductor 31 for detuning said at least one basic element, the planar inductor 31 being electrically connected to the printed circuit board 18g, and disposed outside of the printed circuit board 18g substantially in the same plane as the printed circuit board 18g.

In the embodiments of the invention, the distance between the MR coil 4 and the TMS coil 6 is not uniform across the cap, namely it is the smallest in the center of the hexagonal structure of the MR coil 4, which is also the center of the basic element 17 of the MR coil 4, and it is the largest at the periphery of the hexagonal structure of the MR coil 4.

Note that the stimulation area 6a is the area around the center of the basic element 17, which means that there is some free space 7 between the MR coil 4 and the TMS coil 6 to fill in, which is away from the center of the TMS coil 6. This situation is illustrated in FIGS. 3A and 3B. It has been found that there is enough room for placing the planar PCB 18g outside the basic element 17, as shown on FIGS. 4 and 5, which allows to bring the TMS coil 6 even closer to the tip 72 of the MR coil 4, and therefore closer to the stimulation area 6a, if required.

Figure 10:
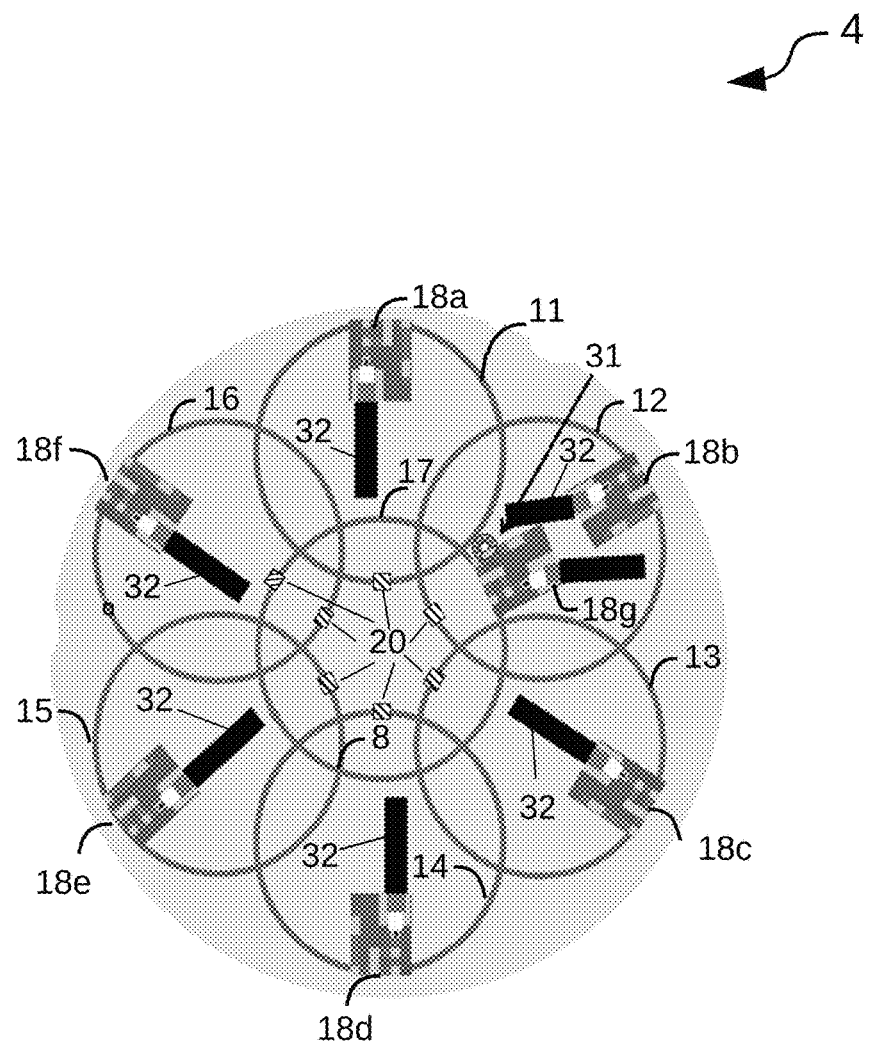
FIG. 10 shows a schematic illustration of an alternative design of the ultra-thin MR coil according to another embodiment of the present invention.

For the other six basic elements 11-16, there is even more free space available between the MR coil 4 and the TMS coil 6, and therefore the planar PCBs 18a-18f of the embodiments of the invention, or even standard PCBs of the prior art, can fit in either outside or inside of their corresponding basic elements 11-16, as shown on FIGS. 4, 5 and 10, respectively. FIG. 10 shows PCBs 18a-18f located inside corresponding basic elements 11-16. Black rectangles 32 protruding from the PCBs 18a-18g represent beginnings of respective coaxial cables 32 shown in FIG. 6.

Thus, the electronic components required for operating the MR coil 4 are conveniently disposed outside the central basic element 17 (and therefore outside the stimulation area 6a) between the cap of the MR coil 4 and a tangent plane 70 at a tip 72.

As a result, the thickness of the MR coil 4 at the tip 72 of the spherical cap 4 has been reduced to about 5 mm, including the thickness of the plastic housing of 3 mm, which is sufficient for the normal operation of the TMS coil 6 through the MR coil 4 in a "sandwiched" arrangement of the embodiments of the invention. If required, the thickness of the MR coil 4 including the plastic housing, in the area where the TMS is applied, can be made smaller than 2 cm, for example, smaller than 15 mm, or smaller than 12 mm, preferably smaller than 10 mm, and more preferably smaller than 7 mm. For example, the thickness of the MR coil can be in a range of 2 mm to 10 mm. With thinner plastic housing for the MR coil 4 and/or thinner wires for the basic elements 11-17 and/or thinner electronic components, the thickness of the MR coil 4 in the stimulation area can be made even smaller than 2 mm. For example, the thickness of the MR coil 4 may be a range of a fraction of a millimeter to 10 mm. In order to bring the MR coil 4 closer to the head 5 of a patient, the plastic housing may be cut out to leave a hole or open space/area in the center of the housing.

Figure 11A:
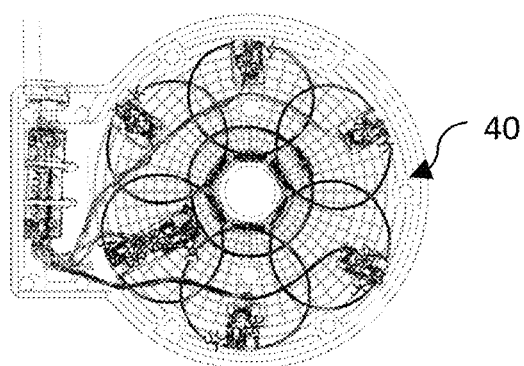
FIG. 11A shows a front view of the MR coil of FIG. 10 packaged in a plastic housing, with a front lid being removed.
Figure 11B:
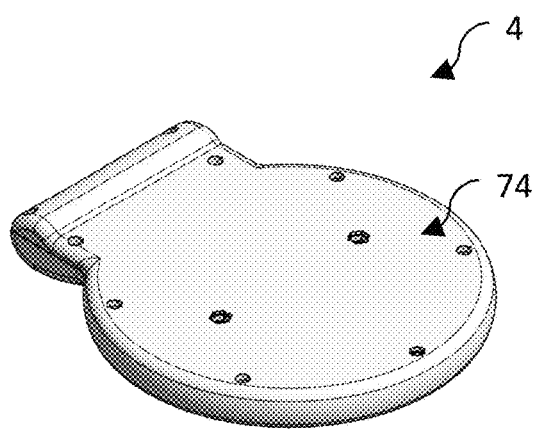
FIG. 11B shows the front view of the MR coil of FIG. 10 packaged in a plastic housing, with the front lid being installed.
Figure 11C:
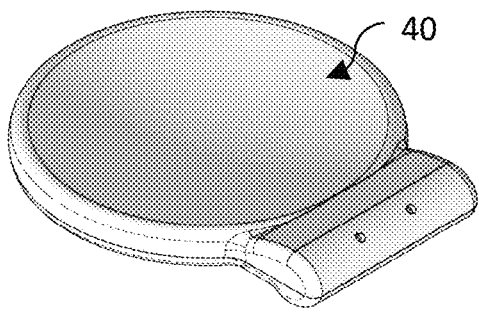
FIG. 11C shows a back view of the MR coil of FIG. 10 packaged in a plastic housing.
Figure 11D:
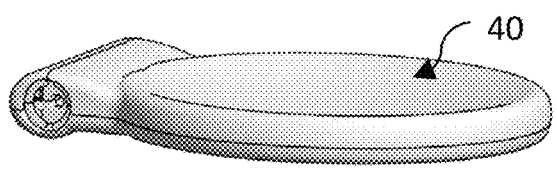
FIG. 11D shows yet another back view of the MR coil of FIG. 11C from a different view point.

The final design of the MR coil 4 packaged in the plastic housing, comprising the plastic base 40 and an upper lid 74, is shown in FIGS. 11a, b, c, d. FIG. 11A shows a front view of the MR coil 4 of FIG. 10 packaged in a plastic housing, with the upper lid 74 being removed; FIG. 11B shows the front view of the MR coil of FIG. 10 packaged in a plastic housing, with the upper lid 74 being installed; FIG. 11C shows a back view of the MR coil of FIG. 10 packaged in a plastic housing; and FIG. 11D shows yet another back view of the MR coil of FIG. 11C from a different view point.

Figure 13A:
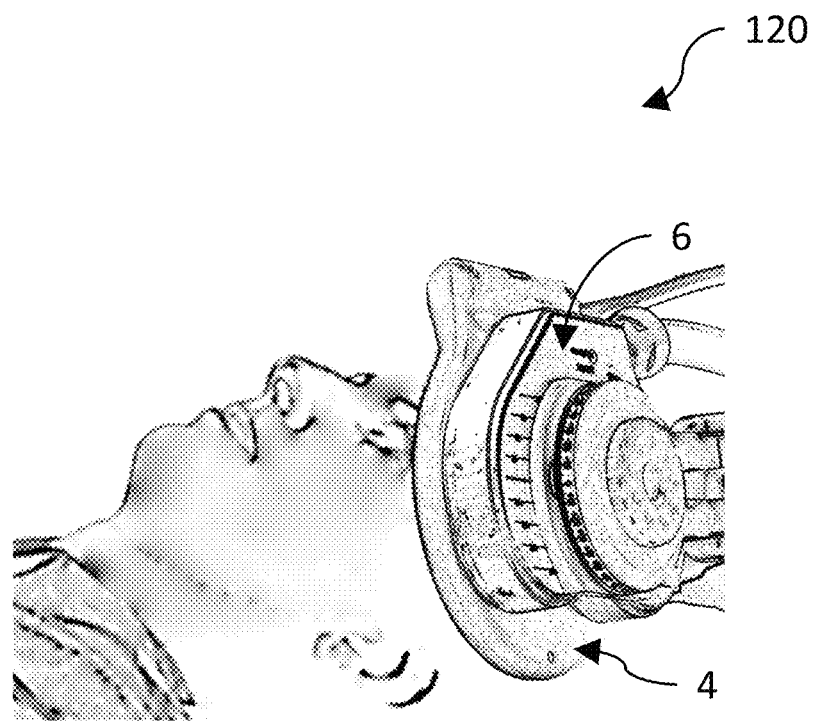
FIG. 13A shows an operational use of the TMS/fMRI system with ultra-thin MR coil of the embodiments of the invention.
Figure 13B:
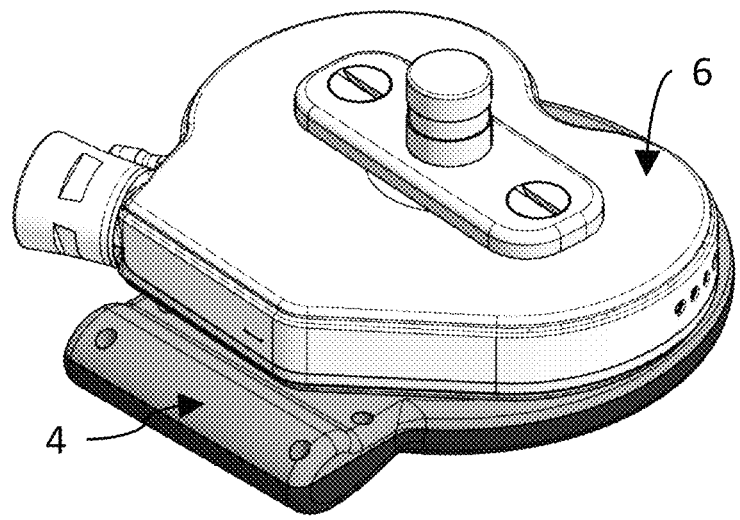
FIG. 13B shows another embodiment of the TMS/fMRI system with ultra-thin MR coil of the embodiments of the invention, with alternative fixing means fixing the TMS coil and the MR coil together.

As discussed above, the TMS coil 6 and the MR coil 4 are spatially arranged such as to allow the TMS to be performed through the MR coil 4, as shown in FIGS. 13A and 13B.

For this reason, the TMS coil 6 and the MR coil 4 have been firmly fastened or fixed together as an integral unit, by mechanical means for preventing motion of the TMS coil 6 with respect to the MR coil 4. Said means for preventing motion to be also referred to as fixing means or fastening means.

At the same time, said fixing or fastening means have been designed so that not to prevent the system 120 from re-targeting the TMS coil 6 and the MR coil 4 to another stimulation/imaging area, as may be required.

The plastic housings of the TMS coil 6 and of the MR coil 4 have been attached together to prevent relative movements.

Figure 12:
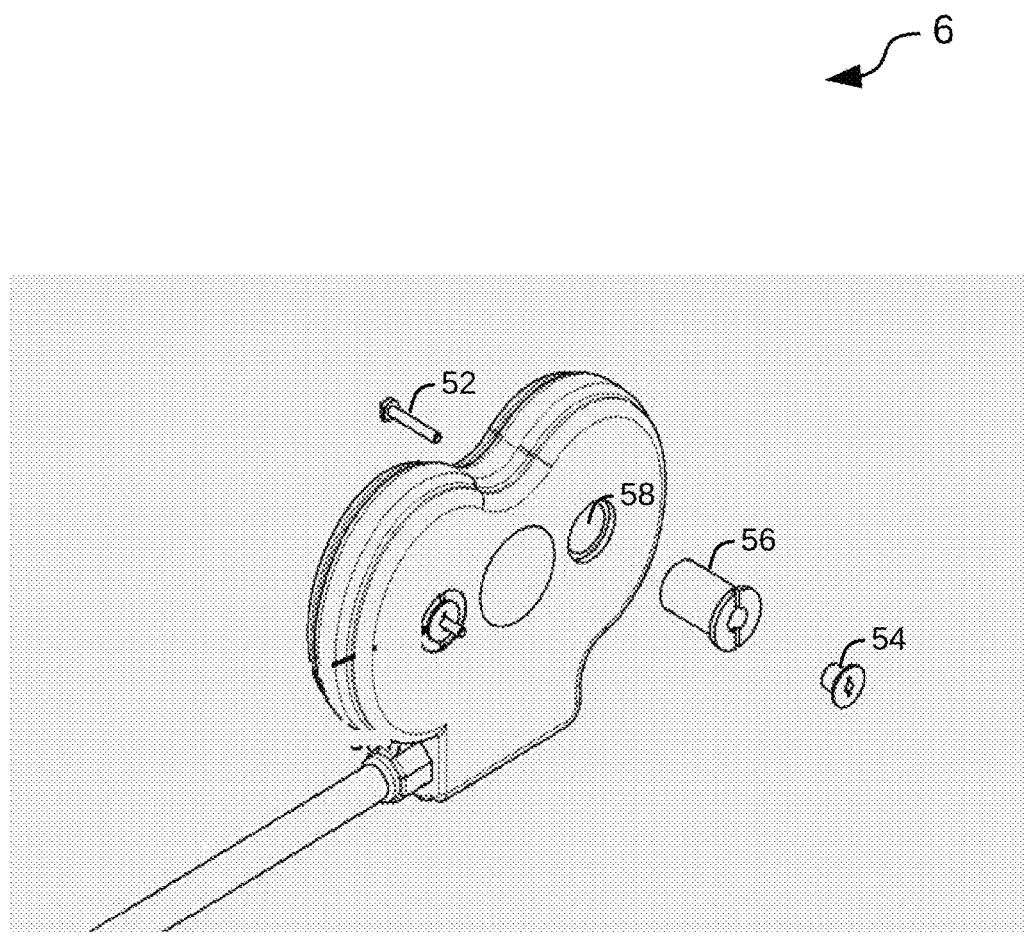
FIG. 12 illustrates fixing means for fastening TMS coil and the MR coil together.

The embodiments of the present invention take advantage of the pre-made holes 58 and the hollow cylindrical insert 56 in the body of commercially available TMS coils, such as those manufactured by MagVenture Inc., Atlanta, Ga., as partially illustrated in FIG. 12. The pre-made holes 58 and the hollow cylindrical insert 56 are intended by the manufacturer to fix the TMS coil to a commercially available TMS coil holder, such as those manufactured by MagVenture Inc., Atlanta, Ga. (not shown). The hollow cylindrical insert 56 has the function of a screw in the hole 58, which has the corresponding thread. The inner side of the hollow cylindrical insert 56 also has a thread for another bolt used to fix the TMS coil to the TMS coil holder (not shown).

FIG. 12 illustrates the process of fixing/fastening the plastic housings of the TMS coil 6 and of the MR coil 4 together according to the embodiments of the present invention.

The TMS coil 6 and the MR coil 4 are fastened/fixed together using a bolt 52, a hollow screw 54, and a nut inside the upper lid 74 of the plastic housing of the MR coil 4. The hollow cylindrical insert 56 is inserted into the hole 58 in the plastic housing of the TMS coil 6, and the bolt 52 goes through the insert 56 and the hollow screw 54 into the nut inside the upper lid 74 of the plastic housing for the MR coil 4 until the MR coil is secured by the nut positioned in the upper lid 74. This ensures, firstly, the robust fastening of the TMS coil 6 and the MR coil 4 together without preventing the existing positioning mechanism of the TMS coil 6 from its intended way of operation, and secondly, the fastening/fixing together of the TMS coil 6 and the MR coil 4 without the need for opening of the upper lid 74 of the MR coil 4. FIGS. 13A and 13B illustrate the TMS coil 6 and MR coil 4 assembled together.

Compactness and ease of repositioning of the TMS/fMRI system 120 of present invention cleared the way for various other embodiments of the present invention, summarized, but not limited to, those shown in FIGS. 14A-14F. FIG. 14A shows a spatial arrangement of the TMS coil and the MR coil, where the MR coil is placed between the head and the TMS coil. FIG. 14B shows a spatial arrangement of the TMS coil and the MR coil, where the MR coil and TMS coil are placed at different positions on the head. FIG. 14C shows a spatial arrangement of the TMS coil and the MR coil of FIG. 14A, with yet an additional MR coil at a different position on the head. FIG. 14D shows two TMS/fMRI systems of FIG. 14A, placed at different positions on the head, for double stimulation. FIG. 14E shows the spatial arrangement of the TMS coil and the MR coil of FIG. 14C, placed on a different area of the head, and FIG. 14F shows the spatial arrangement of the TMS coil and the MR coil of FIG. 14A, placed on a different area of the head.

Certain experimental details related to the MR coil 4 and the TMS/fMRI system 120 of the embodiments of the invention have been provided in the following conference papers by the inventors of this patent application: Oct. 4-6, 2012 Lisbon, P T, 29th Annual Meeting of the ESMRMB (European Society for Magnetic Resonance in Medicine and Biology), poster 352 DOI: 10.1007/s10334-012-0323-x; Mar. 19-21, 2013 Leipzig, G, NBS, 5th International Conference on non-invasive brain stimulation, poster 212, page 307 in the poster list; and Jun. 16-20, 2013, Seattle, Wash., USA, OHBM, Organization for Human Brain Mapping, poster 1027, page 7 in the poster listing, entire contents of the above noted conference papers being incorporated herein by reference and provided in the information disclosure statement submitted herewith.

Numerous modifications and variations can be made to the embodiments described above.

For example, various fixing/fastening means can be used for preventing motion of the TMS coil 6 with respect to the MRI coil 4 during the operation, including glue, tape, scotch, screws, bolts, nails. Alternatively, the plastic housings of the TMS coil 6 and the MR coil 4 can be molded together as one integral unit. As such, any fixing/fastening means would be suitable as long as the TMS coil 6 and the MR coil 4 maintain their positions during operation of the TMS/fMRI system 120.

It is understood that the MR coil 4 may have a larger or smaller number of basic elements than the seven basic elements 11-17 described above. It is also understood that, depending on the size of the basic elements 11-17, each basic element 11-17 may not be divided at all or may be divided into more than two sections, with the capacitors 20 being inserted between the sections.

In the embodiments described above, the TMS coil 6 has been placed on top of the central basic element 17 of the MR coil 4. It is understood that the TMS coil 6 may be also placed against other basic elements as long as the operation of the TMS is maintained.

While basic elements 11-17 have been made in the form of loops, it is also understood that the basic elements 11-17 may have other shapes, if required.

Although the invention has been described with respect to the above noted embodiments, it will be understood by those skilled in the art that the foregoing and various other changes, omissions and deviations in the form and detail thereof may be made without departing from the scope of the invention.

What is claimed is:

1. A system for combined transcranial magnetic stimulation (TMS) and functional magnetic resonance imaging studies, comprising:
    a TMS coil generating a TMS magnetic field for stimulating a stimulation area of an object of medical studies; and
    a coil for magnetic resonance imaging, an MR coil, for MR imaging of the stimulation area and an area surrounding the stimulation area;
    the TMS coil and the MR coil being spatially arranged so that the MR coil is placed between the TMS coil and the stimulation area, and the TMS magnetic field propagates through the MR coil before reaching the stimulation area, thus allowing said stimulating to be performed through the MR coil;
    further comprising:
    fixing means for fixing the TMS coil and the MR coil together as an integral unit to prevent motion of the TMS coil with respect to the MR coil during operation; and
    means for repositioning the integral unit of the TMS coil and the MR coil to different stimulation areas of the object of medical studies.

2. The system of claim 1, further comprising a means for preventing motion of the TMS coil with respect to the MR coil during operation.

3. The system of claim 1, wherein a thickness of the MR coil in the stimulation area is such to ensure the stimulation area is within an operational reach of the TMS coil.

4. The system of claim 3, wherein the thickness of the MR coil in the stimulation area is less than 10 mm.

5. The system of claim 1, wherein the MR coil has a shape substantially corresponding to a shape of the object of medical studies, to which the TMS to be applied.

6. The system of claim 1, wherein the MR coil has a shape of a cap suitable for fitting onto a human head.

7. The system of claim 6, wherein the cap is one of the following:
    a spherical cap, an elliptical cap, a parabolic cap, a hyperbolic cap or a cylindrical cap.

8. The system of claim 6, wherein:
    the MR coil further comprises electronic components for operating the MR coil; and
    those electronic components, which are responsible for controlling an operation of the MR coil in the stimulation area, are disposed outside the stimulation area between the cap and a tangent plane at a tip of the cap.

9. The system of claim 2, wherein:
    the means for preventing motion comprises a base for holding a MR coil; and a shape of the base resembles a shape of the object of medical studies, to which the TMS to be applied.

10. The system of claim 2, wherein the means for preventing the motion comprises a fixing means for fixing the TMS coil and the MR coil togheter as an integral unit.

11. The system of claim 1, wherein the MR coil is a phased array coil, comprising:
    two or more basic elements for processing radio frequency signals generated during the functional magnetic imaging; and
    two or more assemblies of electronic components for respectively operating said two or more basic elements.

12. The system of claim 11, wherein an assembly of electronic components, associated with a basic element in the stimulation area, is disposed outside of the stimulation area.

13. The system of claim 11, wherein assemblies of electronic components, associated with those basic elements, which are outside the stimulation area, are disposed inside respective basic elements.

14. The system of claim 11, wherein assemblies of electronic components, associated with those basic elements, which are outside the stimulation area, are disposed inside respective basic elements.

15. The system of claim 11, wherein an assembly of electronic components associated with a basic element in the stimulation area, comprises a printed circuit board, and a planar inductor for detuning said basic element, the planar inductor being electrically connected to the printed circuit board, and disposed outside of the printed circuit board substantially in the same plane as the printed circuit board.

16. The system of claim 11, wherein basic elements, other than those basic elements in the stimulation area, are arranged to cover a surrounding area around said stimulation area.

17. The system of claim 6, wherein the MR coil comprises seven basic elements, six of which are arranged substantially according to a hexagonal structure, with the remaining seventh basic element being placed substantially in the middle of the hexagonal structure to substantially correspond to the stimulation area.

18. A method for combined transcranial magnetic stimulation (TMS) and functional magnetic resonance imaging (fMRI) studies, the method comprising:
stimulating a stimulation area of an object of medical studies by a TMS coil generating a TMS magnetic field, and performing an fMRI of the stimulation area and an area surrounding the stimulation area by a MR coil, comprising:
spatially arranging the TMS coil and the MR coil to allow said TMS stimulating to be performed through the MR coil, comprising placing the MR coil between the TMS coil and the stimulation area so that the TMS magnetic field propagates through the MR coil before reaching the stimulation area;
further comprising:
fixing the TMS coil and the MR coil together as an integral unit to prevent motion of the TMS coil with respect to the MR coil during operation; and
repositioning the integral unit of the TMS coil and the MR coil to different stimulation areas of the object of medical studies.

19. The method of claim 18, further comprising preventing motion of the TMS coil with respect to the MR coil during operation.

20. The system of claim 11, wherein assemblies of electronic components, associated with those basic elements, which are outside the stimulation area, are disposed outside respective basic elements.

* * * * *

UNITED STATES PATENT AND TRADEMARK OFFICE
CERTIFICATE OF CORRECTION

PATENT NO. : 9,924,889 B2
APPLICATION NO. : 14/045429
DATED : March 27, 2018
INVENTOR(S) : Navarro de Lara et al.

It is certified that error appears in the above-identified patent and that said Letters Patent is hereby corrected as shown below:

Column 13, Line 52 – Column 16, Line 19, delete Claims 1-20 and replace with the following Claims 1-20:

1. A system for combined transcranial magnetic stimulation (TMS) and functional magnetic resonance imaging studies, comprising:
　　a TMS coil generating a TMS magnetic field for stimulating a stimulation area of an object of medical studies; and
　　a coil for magnetic resonance imaging, an MR coil, for MR imaging of the stimulation area and an area surrounding the stimulation area;
　　the TMS coil and the MR coil being spatially arranged so that the MR coil is placed between the TMS coil and the stimulation area, and the TMS magnetic field propagates through the MR coil before reaching the stimulation area, thus allowing said stimulating to be performed through the MR coil.

2. The system of claim 1, further comprising a means for preventing motion of the TMS coil with respect to the MR coil during operation.

3. The system of claim 1, wherein a thickness of the MR coil in the stimulation area is such to ensure the stimulation area is within an operational reach of the TMS coil.

4. The system of claim 3, wherein the thickness of the MR coil in the stimulation area is less than 10 mm.

5. The system of claim 1, wherein the MR coil has a shape substantially corresponding to a shape of the object of medical studies, to which the TMS to be applied.

6. The system of claim 1, wherein the MR coil has a shape of a cap suitable for fitting onto a human head.

Signed and Sealed this
Eighth Day of May, 2018

Andrei Iancu
*Director of the United States Patent and Trademark Office*

7. The system of claim 6, wherein the cap is one of the following:
a spherical cap, an elliptical cap, a parabolic cap, a hyperbolic cap or a cylindrical cap.

8. The system of claim 6, wherein:
the MR coil further comprises electronic components for operating the MR coil; and
those electronic components, which are responsible for controlling an operation of the MR coil in the stimulation area, are disposed outside the stimulation area between the cap and a tangent plane at a tip of the cap.

9. The system of claim 2, wherein:
the means for preventing motion comprises a base for holding a MR coil; and
a shape of the base resembles a shape of the object of medical studies, to which the TMS to be applied.

10. The system of claim 2, wherein the means for preventing the motion comprises a fixing means for fixing the TMS coil and the MR coil together as an integral unit.

11. The system of claim 1, wherein the MR coil is a phased array coil, comprising:
two or more basic elements for processing radio frequency signals generated during the functional magnetic resonance imaging; and
two or more assemblies of electronic components for respectively operating said two or more basic elements.

12. The system of claim 11, wherein an assembly of electronic components, associated with a basic element in the stimulation area, is disposed outside of the stimulation area.

13. The system of claim 11, wherein assemblies of electronic components, associated with those basic elements, which are outside the stimulation area, are disposed inside respective basic elements.

14. The system of claim 11, wherein at least one basic element is divided into two or more sections having section ends, which are connected electrically and mechanically by one or more capacitors, placed between respective section ends, said one or more capacitors being used for suppressing coupling between the basic elements.

15. The system of claim 11, wherein an assembly of electronic components associated with a basic element in the stimulation area, comprises a printed circuit board, and a planar inductor for detuning said basic element, the planar inductor being electrically connected to the printed circuit board, and disposed outside of the printed circuit board substantially in the same plane as the printed circuit board.

16. The system of claim 11, wherein basic elements, other than those basic elements in the stimulation area, are arranged to cover a surrounding area around said stimulation area.

17. The system of claim 6, wherein the MR coil comprises seven basic elements, six of which are arranged substantially according to a hexagonal structure, with the remaining seventh basic element being placed substantially in the middle of the hexagonal structure to substantially correspond to the stimulation area.

18. A method for combined transcranial magnetic stimulation (TMS) and functional magnetic resonance imaging (fMRI) studies, the method comprising:
   stimulating a stimulation area of an object of medical studies by a TMS coil generating a TMS magnetic field, and performing an fMRI of the stimulation area and an area surrounding the stimulation area by a MR coil, comprising:
   spatially arranging the TMS coil and the MR coil to allow said TMS stimulating to be performed through the MR coil, comprising placing the MR coil between the TMS coil and the stimulation area so that the TMS magnetic field propagates through the MR coil before reaching the stimulation area.

19. The method of claim 18, further comprising preventing motion of the TMS coil with respect to the MR coil during operation.

20. The system of claim 11, wherein assemblies of electronic components, associated with those basic elements, which are outside the stimulation area, are disposed outside respective basic elements.

UNITED STATES PATENT AND TRADEMARK OFFICE
CERTIFICATE OF CORRECTION

PATENT NO. : 9,924,889 B2
APPLICATION NO. : 14/045429
DATED : March 27, 2018
INVENTOR(S) : Lucia Isabel Navarro de Lara, Christian Windischberger and Elmar Laistler It is certified that error appears in the above-identified patent and that said Letters Patent is hereby corrected as shown below:

On the Title Page

Item (54) and in the Specification at Column 1, Line 2, in the Title: delete "SIMULATION" and replace with --STIMULATION--

Signed and Sealed this
Second Day of February, 2021

Drew Hirshfeld
*Performing the Functions and Duties of the*
*Under Secretary of Commerce for Intellectual Property and*
*Director of the United States Patent and Trademark Office*